(12) United States Patent
Park

(10) Patent No.: US 10,252,041 B2
(45) Date of Patent: Apr. 9, 2019

(54) PACK FOR SUPPLYING CARBON DIOXIDE TO SKIN AND MANUFACTURING METHOD THEREOF

(71) Applicant: C&TECH CORPORATION, Hwaseong-si (KR)

(72) Inventor: Han-Wook Park, Seoul (KR)

(73) Assignee: C&TECH CORPORATION, Hwaseong-si (KR)

( * ) Notice: Subject to any disclaimer, the term of this patent is extended or adjusted under 35 U.S.C. 154(b) by 209 days.

(21) Appl. No.: 14/385,257

(22) PCT Filed: Sep. 30, 2013

(86) PCT No.: PCT/KR2013/008736
§ 371 (c)(1),
(2) Date: Sep. 15, 2014

(87) PCT Pub. No.: WO2014/069792
PCT Pub. Date: May 8, 2014

(65) Prior Publication Data
US 2015/0250993 A1  Sep. 10, 2015

(30) Foreign Application Priority Data
Oct. 29, 2012 (KR) .................. 10-2012-0120680

(51) Int. Cl.
*A61F 13/00* (2006.01)
*A61M 35/00* (2006.01)
(Continued)

(52) U.S. Cl.
CPC .......... *A61M 35/00* (2013.01); *A61K 8/0208* (2013.01); *A61K 8/19* (2013.01); *A61Q 19/00* (2013.01)

(58) Field of Classification Search
CPC ....... A61M 35/00; A61K 8/0208; A61K 8/19; A61Q 19/00
(Continued)

(56) References Cited

U.S. PATENT DOCUMENTS

2002/0017310 A1* 2/2002 Gruenbacher ......... A01N 25/34
132/320
2005/0244212 A1* 11/2005 Brunner ............... A47L 13/17
401/196
(Continued)

FOREIGN PATENT DOCUMENTS

JP 61207322 9/1986
JP 62-286922 12/1987
(Continued)

OTHER PUBLICATIONS

International Search Report for PCT/ KR2013/ 008736 dated Apr. 2, 2014.

*Primary Examiner* — Andrew J Mensh
(74) *Attorney, Agent, or Firm* — LEX IP MEISTER, PLLC

(57) ABSTRACT

The present invention provides a pack for supplying carbon dioxide to a skin, capable of storing carbonate and acid in an unreacted mixed state without being degenerated according to a change with the passage of long time and easily usable. The pack is formed by successively applying and drying an acid-coated layer and a carbonate-coated layer on one side surface of a non-woven fabric and by laminating a waterproof film on the other side surface thereof. Otherwise, the pack is formed by including a first non-woven fabric configured to have one side surface on which a carbonate-coated layer is formed; a second non-woven fabric configured to have one side surface on which an acid-coated layer is formed; and a waterproof film, wherein the first non-woven fabric and the second non-woven fabric are laminated such that the carbonate-coated layer and the acid-coated layer face each other, and the waterproof film is attached on one outer surface of the lamination.

3 Claims, 2 Drawing Sheets

(51) Int. Cl.
*A61Q 19/00* (2006.01)
*A61K 8/19* (2006.01)
*A61K 8/02* (2006.01)

(58) Field of Classification Search
USPC .......................................................... 604/304
See application file for complete search history.

(56) References Cited

U.S. PATENT DOCUMENTS

2006/0165607 A1\* 7/2006 Tanaka ................. A61K 8/0208
  424/47
2008/0213402 A1\* 9/2008 Tanaka .................... C01B 31/20
  424/700

FOREIGN PATENT DOCUMENTS

| | | |
|---|---|---|
| JP | 05501421 | 3/1993 |
| JP | 4099129 | 6/2008 |
| JP | 4629983 | 2/2011 |
| KR | 1020010031864 | 4/2001 |
| KR | 10-0518698 | 9/2005 |
| KR | 10-0802888 | 2/2008 |
| KR | 1020090049097 | 5/2009 |
| KR | 10-0990947 | 10/2010 |
| KR | 10-1063130 | 8/2011 |
| KR | 10-1092709 | 12/2011 |
| WO | 9924043 | 5/1999 |
| WO | 2004/004745 | 1/2004 |

\* cited by examiner

PACK FOR SUPPLYING CARBON DIOXIDE TO SKIN AND MANUFACTURING METHOD THEREOF

CROSS-REFERENCE TO RELATED APPLICATION

This application is a National Stage application of PCT/KR2013/008736 filed on Sep. 30, 2013, which claims priority to and the benefit of Korean Patent Application No. 10-2012-0120680 filed in the Korean Intellectual Property Office on Oct. 29, 2012, the entire contents of which are incorporated herein by reference.

BACKGROUND OF THE INVENTION (a) Field of the Invention

The present invention relates to a mask pack including a carbon dioxide-containing material to accomplish a skin care effect, and more particularly, to a pack for supplying carbon dioxide to a skin, the pack being in a stable state of being unreacted before being attached on the skin, but supplying carbon dioxide generated by reaction between carbonate and acid to the skin when the pack is attached to the skin and water is applied thereto.

(b) Description of the Related Art

Products for improving cosmetic care or medical treatment by applying carbon dioxide have been conventionally known.

For example, a patent document 1 discloses a fomentation patch that generates carbon dioxide. The fomentation patch is formed of a cloth containing carbonic acid and organic acid. In using of the fomentation, water is supplied thereto, and thus-generated carbon dioxide is applied to a skin.

Since the carbon dioxide is conventionally well known for serving to improve blood circulation, a patent document 2 discloses a foamable solid composition in addition to above-described composition. The foamable solid composition is formed of a mixture of an ascorbic acid-containing component coated with a polymeric substance having an acidic group and a carbonate-containing component coated with a water-soluble neutral polymeric substance. In using of this composition, water is supplied thereto to dissolve the water-soluble polymeric substance coated on the carbonate-containing component and the acidic-group polymeric substance coated on the ascorbic acid-containing component. Accordingly, the carbonate and the ascorbic acid react with each other. This composition is a solid matter, and thus is limited to a bath preparation, foamable powdered drink or snack, a contact lens disinfectant, a detergent for a bathroom etc., and the like, which are necessary for an effect of foaming.

Next, a patent document 3 discloses a solid pharmaceutical composition that generates carbon dioxide by using acid, carbonate, and a thickener (for increasing viscosity). Similarly, patent documents 4 and 5 disclose a carbon oxide-containing viscosity cosmetic composition including various types of compositions using three components of acid, carbonate, and a thickener, such as an aqueous viscous composition for adjusting a generating amount of carbon dioxide caused by the reaction between acid and carbonate by using the thickener.

Next, patent documents 6 and 7 disclose a material for forming carbon dioxide external preparation, including a base agent and a liquid reactant. The base agent includes a non-woven fabric impregnated with a viscous material containing at least an acid and water. The liquid reactant contains at least carbonate, and contacts with the viscous material so as to generate carbon dioxide. In using of the material, the carbon dioxide is applied to a skin by bringing the base agent into contact with a skin and adding the reactant thereto.

Next, a patent document 8 discloses a pack having a skin-contact surface that is formed of a water-permeable material and the opposite surface that is formed of a non-permeable material with a carbon dioxide-containing liquid or a mixture of carbonate and acid being filled therein. In using of the pack, the pack is attached onto a skin and water is added thereinto, and thus carbon dioxide is generated to dissolve it in water and to supply it to the skin, thereby accomplishing an effect of improving blood circulation.

Next, a patent document 9 discloses a skin cosmetic for supplying carbon dioxide, including a carbonate non-aqueous liquid composition and an acidic non-aqueous liquid composition. In using of the skin cosmetic, the carbonate non-aqueous liquid composition and the acidic non-aqueous liquid composition are mixed with each other and water is supplied to the mixture, thereby generating carbon dioxide.

In addition, a patent document 10 discloses that an acid of generating carbon oxide by reacting with carbonate is provided as an acidic polymer.

Patent document 1: Japanese Patent Application Publication No. S62-286922

Patent document 2: Japanese Patent Application Publication No. S61-207322

Patent document 3: Japanese Patent Application Publication No. H05-501421

Patent document 4: International Patent Application Publication No. WO1999-24043

Patent document 6: Korean Patent Registration No. 10-0802888 (Japanese Patent Application Publication No. 2004-307513)

Patent document 7: Korean Patent Registration No. 10-1092709 (Japanese Patent No. 3633930)

Patent document 8: Japanese Patent Application Publication No. 2005-225832

Patent document 9: Japanese Patent Application Publication No. 2005-89357

Patent document 10: Korean Patent Registration No. 10-0990947

The above information disclosed in this Background section is only for enhancement of understanding of the background of the invention and therefore it may contain information that does not form the prior art that is already known in this country to a person of ordinary skill in the art.

SUMMARY OF THE INVENTION

A technique for accomplishing a medical treatment effect or a cosmetic care effect by using a stimulus generated by supplying carbon dioxide to a skin basically uses a method of generating carbon dioxide by mixing carbonate and acid and adding water thereinto.

Both carbonate and acid can exist in a form of powder, and thus it is not difficult to mix carbonate and acid. However, carbonate is a material derived from sodium hydroxide having high deliquescence, and thus it has a property of being melted by adsorbing moistures from the atmosphere. Accordingly, when carbonate and acid are mixed with each other in a form of powder, carbonate absorbing the moistures may react with adjacently contacting acid, thereby generating carbon dioxide unexpectedly.

With this reason, in the aforementioned patent documents, carbonate and acid are separately stored, and they are mixed with each other and water is added thereinto when carbon dioxide is necessary.

However, although carbonate is separately stored, unless the storage is completely sealed, the carbonate still absorbs moistures from the atmosphere to be solidified. Accordingly, as the carbonate is left for a longer time, an amount of carbonate that can react with acid is reduced. Further, it may become a troublesome work to a user to mix carbonate and acid that are separately stored and add water thereinto.

In the meantime, a pack filled with a carbon dioxide-containing liquid or a mixture of carbonate and acid powders is convenient to a user since the pack can be immediately used by adding water to the mixture without mixing them. However, the pack is required to be of a sack-like shape having one side surface formed of a water-permeable material and the other side surface formed of a non-permeable material. Accordingly, the pack is not adequate for mass production.

The present invention has been made in an effort to provide a pack for supplying carbon oxide, having advantages of being capable of storing carbonate and acid in an unreacted mixed state without being degenerated according to a change with the passage of long time, and being adequate for mass production to be manufactured at a low price, in order to accomplish a medical effect or a cosmetic care effect by applying carbon dioxide to a skin.

An exemplary embodiment of the present invention provides a pack for supplying carbon dioxide to a skin, including: a first non-woven fabric configured to have one side surface on which a carbonate-coated layer is formed; a second non-woven fabric configured to have one side surface on which an acid-coated layer is formed; and a waterproof film, wherein the first non-woven fabric and the second non-woven fabric are laminated such that the carbonate-coated layer and the acid-coated layer face each other, and the waterproof film is attached on one outer surface of the lamination.

Herein, the acid-coated layer may be formed by being coated with an acid solution obtained by mixing acid into pure water or water added with a small amount of thickener.

Further, the carbonate-coated layer may be formed by being coated with a carbonate solution obtained by mixing carbonate into one selected from a group including water-soluble oil added with a small amount of thickener; a mixture of anhydrous ethanol added with a small amount of thickener and polyvinyl pyrrolidon; a mixture of the water-soluble oil added with a small amount of thickener, anhydrous ethanol, and the polyvinyl pyrrolidon; and pure water added with a small amount of thickener.

In accordance with the pack having the aforementioned configuration according to the exemplary embodiment of the present invention, non-woven fabrics are used as base materials, and acid and carbonate are respectively coated on one side surfaces of the non-woven fabrics in a form of powder. Accordingly, the pack can be easily conveniently used by simply attaching a cosmetic pack containing a cosmetic essence on a target region and attaching the non-woven fabrics of the pack, having acid and carbonate powders, thereon.

While the pack is used, moistures included in the cosmetic essence permeate into the acid and carbonate powders coated on the non-woven fabrics to dissolve and mix the acid and the carbonate, thereby generating carbon dioxide. However, the thus-generated carbon dioxide is not moved to the outside of the pack at the side of the waterproof film at the action of the waterproof film, but almost all of the carbon dioxide permeates through the non-woven fabrics wet with the cosmetic essence to be supplied to the target region (skin).

In this case, the acid and the carbonate are not directly in contact with the skin of the target region. Accordingly, there is no need to be apprehensive of skin damage.

In addition, the acid and the carbonate are preserved between the non-woven fabrics that are laminated in such a way so as to face each other. Accordingly, there is no possibility that the acid or carbonate powder is peeled off or lost, and thus it is not necessary to be careful about carrying or storing the pack, thereby securing an effective life span of the pack for a long time.

DETAILED DESCRIPTION OF THE EMBODIMENTS

Figure 1:
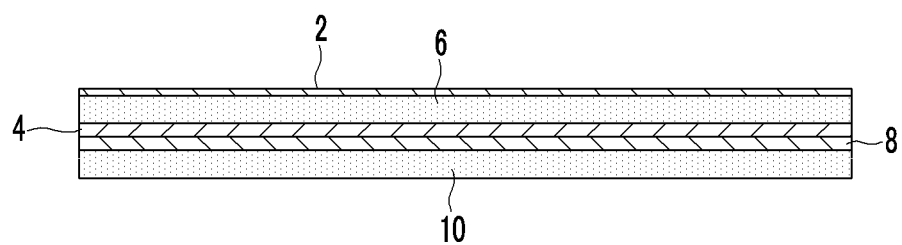
FIG. 1 is a cross sectional side view illustrating the configuration of a pack according to an exemplary embodiment of the present invention.

As shown in FIG. 1, a pack according to an exemplary embodiment of the present invention is formed by laminating a first non-woven fabric 6 having one external side surface on which a waterproof film 2 is attached and the other side surface on which a carbonate-coated layer 4 is coated, and a second non-woven fabric 10 having one side surface that faces the carbonate-coated layer 4 and is coated with an acid-coated layer 8.

Herein, the carbonate-coated layer 6 is coated with a solution obtained by mixing carbonate into purified water or purified water added with a small amount of thickener at a ratio of 1 to 1.

Carbonate is precipitated after being dissolved in the purified water. However, as a small amount of thickener is added thereinto, the viscosity of the purified water is increased. Accordingly, the carbonate is maintained to be uniformly mixed without being precipitated.

The thickener that can be applied to the present invention is not limited to a specific one. In this exemplary embodiment, a small amount, e.g., 1.5 wt % of cellulose gum was applied to carbonate.

Further, the acid-coated layer 8 was easily dissolved in water without precipitations, and thus a mixed liquid that was dissolved in purified water was used.

When the waterproof film 2 and the second non-woven fabric 10 are adhered to opposite surfaces of the non-woven fabric 6, a medical adhesive may be used. However, the best method is to use an ultrasonic wave in view of the efficiency and cost of a manufacturing process.

In the pack having the aforementioned configuration according to the present exemplary embodiment, even when the carbonate-coated layer 4 is provided in a form of powder after being coated and dried, the carbonate-coated layer 4 is preserved between the first non-woven fabric 6 and the second non-woven fabric 10. Accordingly, there is no possibility of being peeled off or lost, and thus it is not necessary to be careful about carrying the pack so that it is easy to deal with the pack. In addition, even after a long period of storage, the effect may not be deteriorated.

Further, in using of the pack, when typical cosmetic essence or water is applied to a target region and the pack is attached thereto, moistures permeate into the inside of the pack through the second non-woven fabric 10 to enable carbonate and acid to generate carbon dioxide. However, the thus-generated carbon dioxide is blocked by the waterproof film 2, and thus almost all of the carbon dioxide permeates through the second non-woven fabric 10 and is supplied to the target region. In this case, the target region is covered with the second non-woven fabric 10 of the pack according to the present exemplary embodiment, and thus carbonate components and acid components are directly prevented from coming into brought with the target region, thereby suppressing skin damages or allergies. As a result, the pack is optimized for skin management using carbon oxide.

Figure 2:
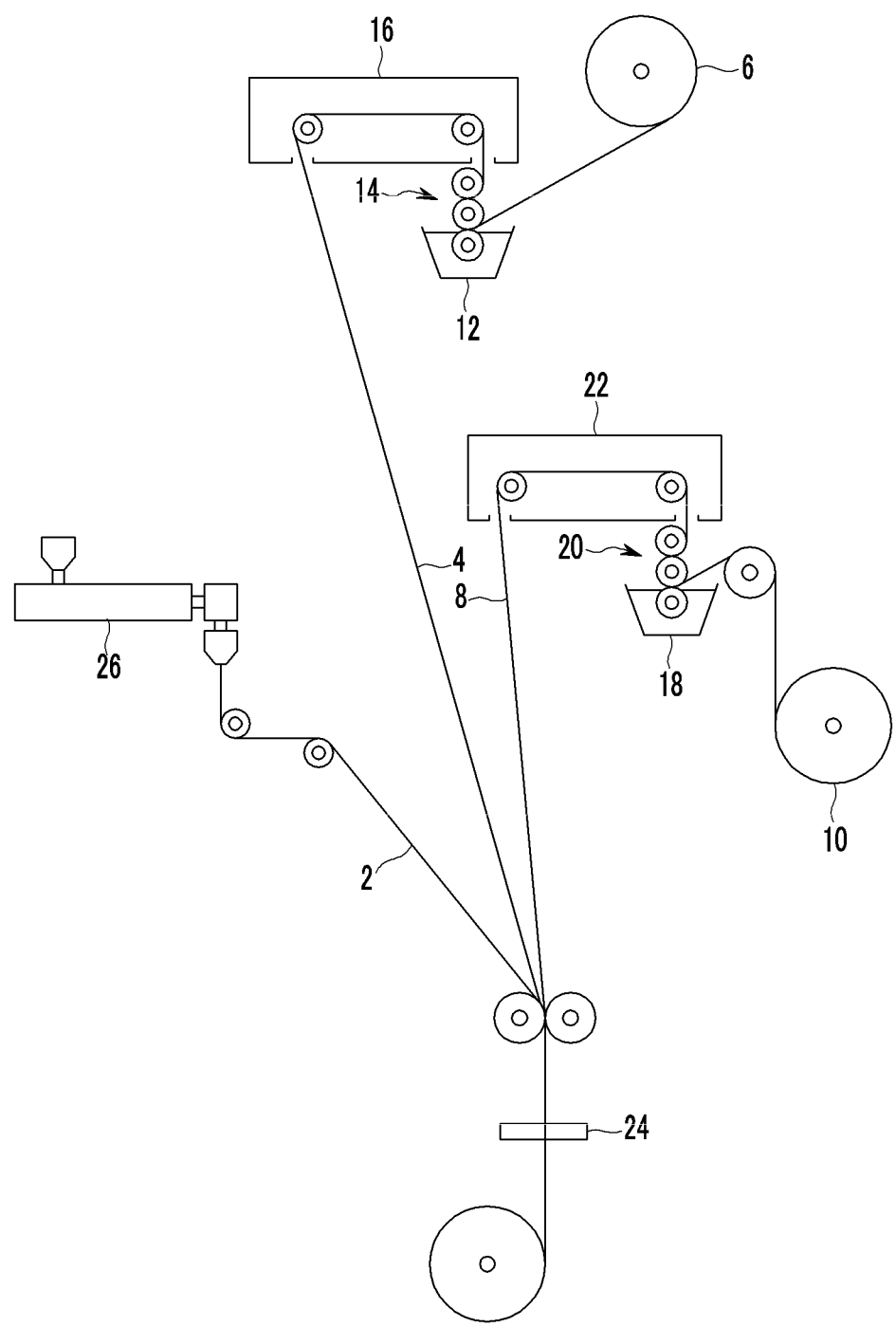
FIG. 2 is a schematic diagram illustrating an example of a pack manufacturing method according to the exemplary embodiment of the present invention.

The pack according to the present exemplary embodiment may be manufactured by using a manufacturing process illustrated in FIG. 2.

In a first coating bath 12 in which a carbonate solution is stored, the first non-woven fabric 6 passes through a carbonate coating roll unit 14 to coat the carbonate solution on one side surface of the first non-woven fabric 6 in a roll-coating method or in a gravure method. Then, the first non-woven fabric 6 coated with carbonate is dried when passing through a first drying furnace 16. As a result, the carbonate-coated layer 4 is provided in a form of powder on one side surface of the first non-woven fabric 6.

In the meantime, in a second coating bath 18 in which an acid solution is stored, the second non-woven fabric 10 passes through an acid coating roll unit 20 to coat the acid solution on one side surface of the second non-woven fabric 10 in the roll-coating method or in the gravure method. Then, the second non-woven fabric 10 coated with acid is dried when passing through a second drying furnace 22. As a result, the acid-coated layer 8 is provided in a form of powder on one side surface of the second non-woven fabric 10.

As such, the first non-woven fabric 6 formed with the carbonate-coated layer 4 and the second non-woven fabric 10 formed with the acid-coated layer 8 are laminated and pass through an ultrasonic welder 24 to be adhered to each other. In this case, the waterproof film 2 supplied through a typical T-die 26 is laminated on an outer surface of the first non-woven fabric 6, i.e., an opposite surface thereof to the carbonate-coated layer 4, and passes through the ultrasonic welder 24. As a result, the pack shown in FIG. 1 can be manufactured.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

DESCRIPTION OF SYMBOLS

2: waterproof film
4: carbonate-coated layer
6: non-woven fabric
8: acid-coated layer
10: non-woven fabric
12: first coating bath
14: first coating roll unit
16: first drying furnace
18: second coating bath
20: second coating roll unit
22: second drying furnace
24: ultrasonic welder

What is claimed is:

1. A pack for supplying carbon dioxide to a skin, the pack comprising:
    a waterproof film;
    a first non-woven fabric disposed below the waterproof film and adhered to the waterproof film;
    a carbonate-coated layer disposed below the first non-woven fabric and adhered to the first non-woven fabric;
    an acid-coated layer disposed below the carbonate-coated layer as a separate layer than the carbonate-coated layer and adhered to the carbonate-coated layer, and
    a second non-woven fabric disposed below the acid-coated layer and adhered to the acid-coated layer,
    wherein, prior to the pack being used, the carbonate-coated layer and the acid-coated layer are in a form of dried powder and the first non-woven fabric and the second non-woven fabric are laminated, and
    wherein, when the pack is used, moisture permeates into the pack through the second non-woven fabric to mix with the carbonate-coated layer and the acid-coated layer generating carbon dioxide, and a carbonate of the carbonate-coated layer and an acid of the acid-coated layer do not directly contact the skin.

2. The pack of claim 1, wherein the acid-coated layer is a mixture of an acid and pure water or a mixture of an acid, water, and a small amount of thickener.

3. The pack of claim 1, wherein the carbonate-coated layer is a mixture of carbonate and one selected from a group including a mixture of water-soluble oil and a small amount of thickener; a mixture of anhydrous ethanol, a small amount of thickener, and polyvinyl pyrrolidon; a mixture of the water-soluble oil, a small amount of thickener, anhydrous ethanol, and polyvinyl pyrrolidon; and a mixture of pure water and a small amount of thickener.

* * * * *